US005795883A

United States Patent [19]
Hesch et al.

[11] Patent Number: 5,795,883
[45] Date of Patent: Aug. 18, 1998

[54] ANDROGENS AND ANABOLIC AGENTS

[75] Inventors: Rolf-Dieter Hesch, Constance; Michael Oettel, Jena; Peter Droescher, Weimar; Sigfrid Schwarz, Jena; Bernd Menzenbach, Jena; Wolfgang Römer, Jena; Günter Kaufmann, Jena; Jens Schröder, Jena, all of Germany

[73] Assignee: Jenapharm GmbH, Jena, Germany

[21] Appl. No.: 537,725

[22] PCT Filed: Mar. 18, 1994

[86] PCT No.: PCT/DE94/00316

§ 371 Date: Nov. 6, 1995

§ 102(e) Date: Nov. 6, 1995

[87] PCT Pub. No.: WO94/24146

PCT Pub. Date: Oct. 27, 1994

[30] Foreign Application Priority Data

Apr. 13, 1993 [DE] Germany .......................... 43 12 034.2

[51] Int. Cl.$^6$ .............................. A61K 31/58; C07J 17/00
[52] U.S. Cl. .............................. 514/172; 540/94
[58] Field of Search .............................. 552/639, 638, 552/614; 514/177, 178, 179, 180, 181, 172; 540/94

[56] References Cited

U.S. PATENT DOCUMENTS 5,202,316  4/1993  Claussner et al. ..................... 514/176

FOREIGN PATENT DOCUMENTS 2 247 390  3/1974  Germany .
87/07895  12/1987  WIPO .

OTHER PUBLICATIONS

BMJ Publications, "Androgens and Anabolic Steroids", British Med. J., vol. 1, 165–167, 1969.
Patel, Pharmacotherapy of cognitive impairment in Alzheimer's disease: A review. J. Geriatric Psychiatry and Neurology 8: 81–95, 1995.
Stein, Internal Medicine, 4th edition, chapters 71–72, pp. 699–715, 1995.
Role of Reactive Oxygen Species in Biological Processes, H. Sies, Klinisce Wochen Schrift, 1991.
Molecular and Cellular Biochemistry III, 1992, pp. 143–147, S. Chatterjee, "Role of Oxidized human plasma low density lipoproteins . . . ".
Journal of Cardiovascular Pharmacology, 1992, B. Weisser, et al., "Oxidized Low–Density Lipoproteins in Atherogenesis . . . ".
Klinische Wochenschrift, 1991, pp. 1032–1038, H.F. Hoff, et al, "Oxidation of LDL: Role in Atherogenesis".
Klinsche Wochenschrift, 1991, pp. 1039–1045, K.L.H. Carpenter, et al, "Oxygen Radicals and Atherosclerosis".
Annuals of Internal Medicine, vol. 116, No. 12 (Part 1), C.J. Bagatell, et al, "Physiologic Testosterone Levels in Normal Men . . . ".
Medicine and Science in Sports and Exercise, 1992, vol. 24, No. 3, Andrew S. Weyrich, et al, "The effects of testosterone on lipids . . . ".
Clinical and Experimental Pharmacology & Physiology, 1986, pp. 513–518, D.M. Crist, et al.
Int. Journal of Sports Med. 6, 1985, pp. 139–144, M. Alen, et al, "Serum Lipids in Power Athletes . . . ".
Int. J Fertil, 37, 1992, pp. 83–92, M.D.G. Gillmer, "Mechanism of Action/Effects of Androgens on Lipid Metabolism".
Bailliere's Clinical Andocrinology and Metabolism, 1990, vol. 4, No. 4, David Crook, et al, "Endocrine Control of Plasma Lipoprotein Metabolsim . . . ".
Godsland, et al, "Sex, Plasma Lipoproteins, and Atherosclerosis . . . ", 1987, pp. 1467–1503.
Maturitas 11 (1989), pp. 305–317, Hassager, et al "Nandrolone Decanoate Treatment of Post–Menopausal Osteoperosis . . . ".

Primary Examiner—Allen J. Robinson
Assistant Examiner—Barbara Badio
Attorney, Agent, or Firm—Michael J. Striker

[57] ABSTRACT

Novel androgens having one or more substituents providing radical trapping properties are disclosed as useful in methods of treating androgen deficiency in man, benign prostate hypotropy and carcinoma of the prostate, osteoporosis, vascular disease-induced or ischemically-induced cerebral edemas, subarachnoid hemorrhages, ischemic shock, cerebral insult, Parkinson's disease and Alzheimer's disease. The androgen compound used for treating androgen deficiency in man has a steroid ring with an α-tocopherol group or a trolox group substituent.

12 Claims, No Drawings

ANDROGENS AND ANABOLIC AGENTS

This application is a 371 of PCT/DE94/00316 filed Mar. 18, 1994.

BACKGROUND OF THE INVENTION

The invention relates to novel androgens and derivatives and analogs thereof, such as anabolic agents, and to methods of using them.

Male hormones, that is, androgens, such as testosterone and dihydrotestosterone and various esters of testosterone, such as testosterone proprionate, testosterone enanthate, testosterone undecanoate or testosterone bucyclate, or derivatives and analogs, such as anabolic agents like mesterolone, are used in man to treat an androgen deficiency. This may be a primary androgen deficiency (testicular insufficiency), secondary androgen deficiency (hypothalamo-hypophyseal insufficiency) or "complex androgen deficiency" (hypothalamo-hypophyseal-testicular) in the aging male. This latter is also known as "male menopause", or more recently, "andropause".

Complex androgen deficiency in the male leads to an existential disturbance as a consequence of which, at an indefinite time but typically from the age of 45 on, signs of male hormone deficiency can arise, with continuously varying symptoms. These signs are predominantly in the form of mood fluctuations, along with psychosomatic performance problems. Often these problems are accompanied by increasing impotentia coeundi, as a consequence of which signs of depression and loss of self-esteem often occur; mental alertness can be impaired as well. Spermatogenesis is affected less severely. The drop in anabolic effectiveness of the androgens, often in combination with a lack of exercise, leads to increasing atrophy of the musculature. Bone mass is also reduced as a result, along the lines of osteoporosis. Hematopoiesis can be lessened as well.

It is notable that the occurrence of benign enlargement or hypertrophy of the prostate has a course that is parallel with these changes, although in that disease an increased enzymatic conversion of testosterone to dihydrotestosterone in the prostate is suspected. An analogy with iodine deficiency of the thyroid gland can be suspected, in which along with the formation of a tissue hyperplasia known as goiter, triiodothyronine is increasingly formed enzymatically from the reduced thyroxin substrate in the thyroid gland. A testosterone deficiency in the prostate can also increase the formation of dihydrotestosterone by increased enzymatic conversion, which represents a tissue hyperplastic stimulus in the prostate, resulting in the formation of tissue hyperplasia known as benign enlargement of the prostate. According to this hypothesis, benign enlargement of the prostate could be predominantly the result of a testosterone deficiency. The causation by androgens, and especially the metabolism of testosterone into dihydrotestosterone, in conjunction with the occurrence of arteriosclerosis, has not yet been explained in all its details. Yet precisely this causality should be paid particular attention in deciding whether to institute male hormone replacement.

Overall there is a need for more precise knowledge of the action of androgens in the aging male, but there is also a need for androgen derivatives that do not develop unfavorable effects in essential male target organs, such as the prostate and the vascular system.

Because of the lack of certainty about the safety of the effects and side effects of testosterone and its derivatives, including the anabolic agents, the indications for therapy or replacement (hormone replacement) with male hormones and their analogs are thus far only inadequately defined and authorized by the Bundesgesundheitsamt [Federal German Health Office].

Androgens are used for replacement in the human male only when primary or secondary androgen deficiency is found with certainty, and is generally done in the form of monthly depot injections. Other preparations, for instance for transdermal application, are in development. Oral replacement of male hormones is also being employed. The so-called first-pass effect of the action of the hormones on metabolism in the liver and protein synthesis (for instance, lipoprotein synthesis with a change in lipid metabolism) is observed in particular. Overall, satisfactory replacement even with this indication is successful in only a relatively small proportion of those affected. For instance, osteoporosis is not prevented in all cases in men with this replacement therapy, and potency problems often persist.

In the case of complex hormone deficiency syndrome in the human male, replacement is not yet possible, especially in view of the uncertain effects and unpredictable side effects.

Androgen therapy with anabolic agents for therapy of postmenopausal osteoporosis in women (Hassager et al, Maturitas 1:305–317, 1989) is no longer allowed in Germany by the Federal German Health Office on account of its inadequate effectiveness and possible side effects.

In long-term use of androgens in the male, a distinction must be made between therapy and replacement. Therapy typically requires relatively high doses. Replacement is preferentially done with dosages that are near the rate of production of the natural hormone. The mode of administration must also be considered, since the steroidal effect of injection preparations for therapy and replacement, as well as that of the anabolic agents (androgen-effective steroid hormones) differs from that of the same substances transmitted transdermally or orally. This affects the liver metabolism primarily, but also the direct receptor-mediated effect on androgen-dependent tissues, such as the prostate, the vascular system and the bones.

At the onset of puberty, the blood serum concentrations of high-density lipoproteins (HDL cholesterol) in the human male drop, and there is a negative correlation with the rising testosterone secretion (Godsland et al, A. Heart J. 114:1467–1503, 1987).

The exogenous delivery of androgens and anabolic agents causes the following changes in the lipid or lipoprotein blood concentration: a drop in triglyceride from an alteration in VLDL secretion or VLDL metabolism, a drop in HDL and especially $HDL_2$ values; influence on apoprotein A-I synthesis with a drop in lipoprotein values, and finally an increase in LDL cholesterol concentrations (D. Crook, M. Seed, Baillieres, Clin. Endocrinol. Metab. 4:851–875, 1990; M. D. Gillmer, Int. J. Fert. 37:Suppl. 2, 83–92, 1992; M. Alen et al, Int. J. Sports Med. 6:139–144, 1985; D. M. Christ et al, Clin. Exptl. Pharmacol. Physiol. 13:513–518, 1986). In parallel with the drop in HDL cholesterol and the rise in LDL cholesterol, the exogenous delivery of testosterone raises the plasma concentrations of thromboxane B2 (A. S. Weyrich et al, Med. Sci. Sports Exercise 24:333–338, 1992).

On the other hand, hypogonadism induced by gonadotropin releasing hormone antagonists leads to a significant rise in HDL cholesterol, including $HDL_2$ and $HDL_3$, and of apoprotein A-I (C. J. Bagatell et al, Ann. Int. Med. 116:967–973, 1992).

The rise in low-density lipoproteins (LDL cholesterol) under the influence of testosterone correlates well with the occurrence and progress of arteriosclerotic changes. Oxidized LDL directly attacks the vascular muscle and promotes plaque formation (K. L. H. Carpenter et al, Klin. Wochenschr. |Clinical Weekly| 69:1039–1045, 1991; H. F. Hoff, J. A. O'Neil, Klin. Wochenschr. 69:1032–1038, 1991; B. Weisser et al, J. Cardiovasc. Pharmacol. 19:Suppl. 2, S4–S7, 1992; S. Chatterjes, Mol. Cell. Biochem. 11:143–147, 1992). The oxidation of LDL is caused by free oxygen radicals and hydrogen peroxides (H. Sies, Klin. Wochenschr. 69:965–968, 1991).

The state of current scientific knowledge shows that androgens per se already physiologically had an unfavorable influence on the development of arteriosclerosis in the male. This circumstance is partly responsible for the shorter life span of the male compared with the female. This physiological effect is reinforced in the current androgen replacement and androgen therapy and anabolic agent therapy. In view of the health and social significance of cardiovascular diseases in western culture, broad androgen replacement in the male has therefore not yet been possible. Anabolic agent therapy for various indications was considered dangerous.

SUMMARY OF THE INVENTION

It is therefore the object of the invention to make available androgens or anabolic agents that exhibit the above-described negative effects to only a greatly reduced extent if at all, so that they can be used suitably for treating various diseases without the above-described unfavorable effects on the occurrence or worsening of arteriosclerosis.

According to the invention, this object is attained by furnishing novel androgen and anabolic agent types that are distinguished by at least one substituent or substituent grouping that has radical trapping properties. While maintaining the fundamental direction of androgenic/anabolic effect, an unexpectedly high inhibition of lipid peroxidation is unexpectedly attained. This special spectrum of effectiveness is entirely unexpected and atypical for androgens.

Without restriction thereto, the invention will be described in further detail below taking one of the most important androgens, namely testosterone, as an example. The general structural formula of testosterone is as follows:

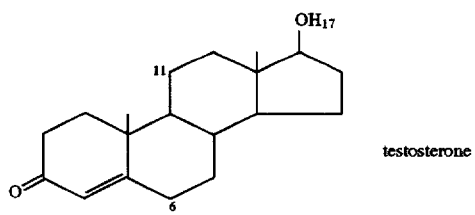

testosterone

Although in principle the introduction of a substituent at any arbitrary position of the molecule appears possible and useful, it has been demonstrated that especially advantageous effects can be attained with substituents at the ring positions 6, 11 or 17 of the steroid ring system.

Especially preferred substituents and substituent groupings are:

substituted or unsubstituted phenols, substituted or unsubstituted aromatic amines, sulfides, disulfides and thiols; croman-6-ols, especially α-tocopherol and trolox, including their derivatives and esters; ascorbic acid, including its esters; 2,4-dipyrrolidino-6-N-piperidinopyrimidine, including its N'-alkyl and N'-acyl derivatives; cysteine; cysteamine; melanines, and vicinal hydroxy groups.

By way of example, a few compounds will be listed below, in which an aromatic sulfide functions as a radical trapping group:

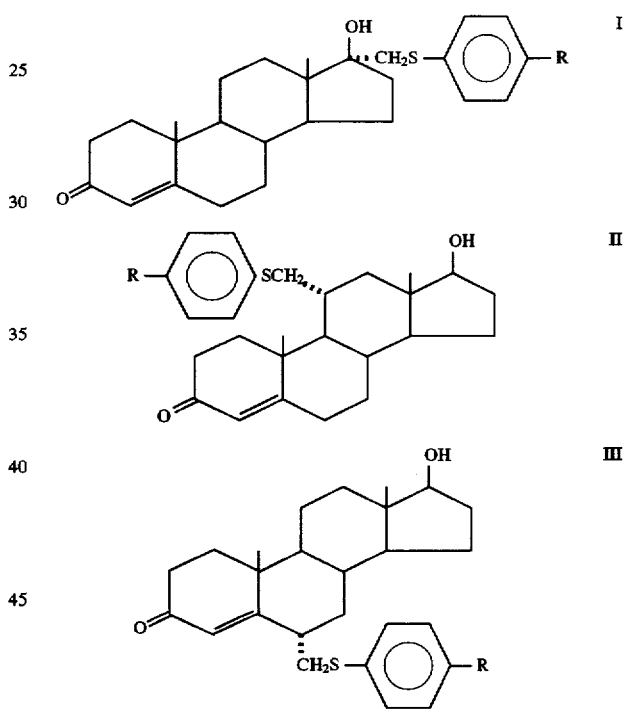

Other examples with different substituents or the substituents named above at the testosterone basic ring system are as follows:

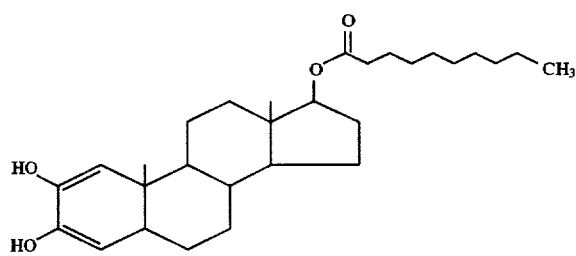

1, 2-dihydroxytestosterone decanoate

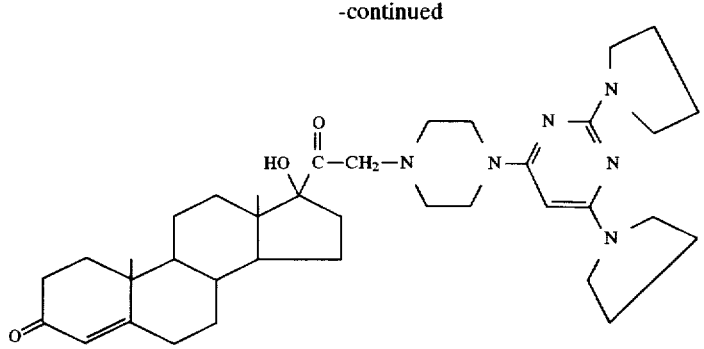

V

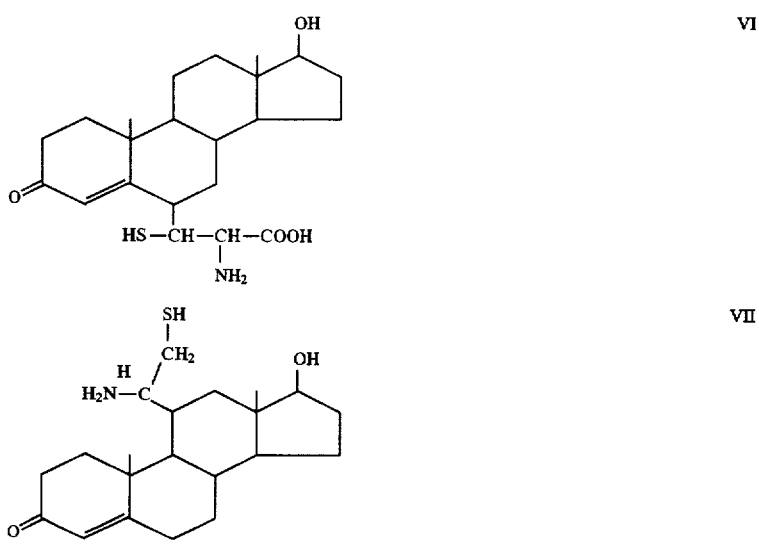

VI

VII

However, it is also noted that comparable results can be attained with other substituents and substituent groupings and with substituents at different positions as well, as long as the principal radical trapping property of the substituent or substituents is assured. This implicitly naturally also means that other substituents besides those named above can be considered, including both already known compounds with radical trapping properties and future novel compounds in which this property is ascertained.

The preparation of the compounds according to the invention can be done by processes known per se in organic chemistry. A broad range of reaction routes and reaction conditions, which are within the competence and knowledge of one of average skill in the art, is possible.

The invention also relates to the use of the compounds according to the invention for androgen or anabolic agent replacement or therapy for treating an androgen deficiency, and other uses, as defined by dependent claims 5–13.

From the series of compounds listed above by way of example, a few of each were studied in comparison with α-tocopherol with a view to their effect on lipid peroxidation. $ED_{50}$ values of from 10.0 to 0.1 μM were found.

Measurement of the androgen receptor bond was done by competitive binding of the 3H-marked synthetic androgen RU1881 and the compound to be tested to the androgen receptor in prostate cytosol of castrated male rats at 0° C. It was found that at a dosage range from 0.1 pg to 1000 pg, the novel substance is capable of replacing 50% of the radio-active comparison substances used at the receptor.

Testing for androgens and anabolic activity was done as follows:

Male Wistar rats with a body mass between 35 and 45 g received the total steroid doses, distributed into six daily doses, in an injection volume of 0.2 ml per animal per day subcutaneously. 24 h after the last injection, the fully anesthetized animals were killed; the testes (an indicator of antigonadotropic effect), levator ani muscle (indicator of the anabolic effect), ventral prostate and glandula vesiculosa (indicators of androgenic action) were extracted, immediately freed of attached connective tissue and vessels, and weighed.

It was found that in a dosage range of from 0.1 to 50 μg per g of animal body weight, a pronounced androgenic effect is ascertainable.

In addition, the inhibiting effects on the oxidation of LDL cholesterol were studied and it was found that in a dosage range of from 1 pmol to 100 nmol, an up to 50% inhibition of the oxidation of LDL cholesterol was attainable.

Finally, investigations of the inhibition of postischemic cortical neural necrosis in the gerbil were done in the following way:

Male Mongolian gerbils (Meriones unguiculatus) weighing 55 to 65 g were anesthetized with methoxyflurane.

After a medial mid-neck incision, the right carotid artery was isolated and closed with a microaneurysm clamp. The wound was then closed with surgical staples. The animals were then placed in individual cages. The following signs of cerebral ischemia were recorded: circling motions, inability to run, ptosis, torso rolling, opisthotonos, loss of the standing-up reflex, convulsive states. Animals that did not exhibit these symptoms one hour after carotid closure were excluded from the further course of the experiment. 3 h after carotid closure, the animals were reanesthetized with methoxyflurane; the carotid clamp was removed, and care was taken that re-perfusion took place through the previously closed carotid artery. The animals received the test substances intraperitoneally ten minutes prior to the carotid closure and immediately after the carotid opening. After re-perfusion, the gerbils were again anesthetized, and intracardial infusion was done with the following fixative solution: 10% formaldehyde, 10% glacial acetic acid and 80% methanol. The fixed brains were removed and embedded in paraffin. Histologic sections (5 μm thick and 1.4 to 3.0 ml behind the bregma) were placed on glass slides and stained with cresyl violet. Unaltered neurons stain with cresyl violet and can be counted, using 320-power microscopic enlargement. The direct comparison was always made between the normal and the ischemic hemisphere.

In a range from 0.5 to 50 mg/kg of body weight, a protective function against neuron degeneration by carotid closure was found.

From the above results it can be seen that it becomes possible within the scope of the present invention to prepare androgens and anabolic agents, with an essentially preserved fundamental direction of action, with high inhibition of lipid peroxidation.

This makes androgen or anabolic agent replacement or therapy possible for treating an androgen deficiency, such as in hypergonadal men or men undergoing male menopause or so-called andropause, which can be done without increasing the risk to the heart and circulatory system.

Logically the same applies to women during menopause or in postmenopause as well. The androgens and anabolic agents according to the invention can be used above all to overcome depressive states and for prophylaxis and therapy for osteoporosis, with and without combination with estrogen and/or progestogens, without this being attained at the cost of an increase in the risk to the heart and circulatory system.

Testosterone-based compounds can be used in particular to treat benign hypertrophy of the prostate and carcinoma of the prostate.

In this connection it is noted that free oxygen radicals play a substantial etiopathological role in the context, among others, of vascular disease- or ischemically-induced cerebral edemas, in subarachnoid hemorrhages, in ischemic shock, in cerebral insult, in certain forms of asthma, in Alzheimer's disease and Parkinson's disease, in organ transplantation, and in androgen-dependent or non-androgen-dependent malignant neoplasms. There are in fact clear indications that the compounds according to the invention have a therapeutic potential in these areas as well.

We claim:

1. A compound selected from the group consisting of androgens having at least one substituent providing radical trapping properties, wherein said at least one substituent is selected from the group consisting of an α-tocopherol group and a trolox group.

2. A method of treating androgen deficiency comprising administering an effective amount of an androgen having at least one substituent providing radical trapping properties to a man suffering from androgen deficiency, wherein said at least one substituent is selected from the group consisting of an α-tocopherol group and a trolox group.

3. A method of treating prostate hypotrophy and prostate carcinoma, said method comprising administering an effective amount of an androgen having at least one substituent providing radical trapping properties to a man suffering from said prostate hypotrophy and prostate carcinoma, wherein said at least one substituent is selected from the group consisting of an α-tocopherol group and a trolox group.

4. A method of treating osteoporosis, said method comprising administering an effective amount of an androgen having at least one substituent providing radical trapping properties to an individual suffering from said osteoporosis, wherein said at least one substituent is selected from the group consisting of an α-tocopherol group and a trolox group.

5. The method as defined in claim 4, further comprising administering together with said androgen at least one member selected from the group consisting of estrogen and progestogens to said individual.

6. The method as defined in claim 4, wherein said individual is a woman and said osteoporosis is postmenopausal osteoporosis.

7. A method of treating vascular disease-induced or ischemically-induced cerebral edemas, subarachnoid hemorrhages, ischemic shock and cerebral insult, said method comprising administering an effective amount of an androgen having at least one substituent providing radical trapping properties to an individual, wherein said at least one substituent is selected from the group consisting of an α-tocopherol group and a trolox group.

8. A method of treating asthma, said method comprising administering an effective amount of an androgen having at least one substituent providing radical trapping properties to an individual suffering from said asthma, wherein said at least one substituent is selected from the group consisting of an α-tocopherol group and a trolox group.

9. A method of treating Alzheimer's disease, said method comprising administering an effective amount of an androgen having at least one substituent providing radical trapping properties to an individual suffering from said Alzheimer's disease, wherein said at least one substituent is selected from the group consisting of an α-tocopherol group and a trolox group.

10. A method of treating Parkinson's disease, said method comprising administering an effective amount of an androgen having at least one substituent providing radical trapping properties to an individual suffering from said Parkinson's disease, wherein said at least one substituent is selected from the group consisting of an α-tocopherol group and a trolox group.

11. A method of preventing rejection of an organ transplanted during an organ transplantation procedure, said method comprising administering an effective amount of an androgen having at least one substituent providing radical trapping properties to an individual having said transplantation procedure, wherein said at least one substituent is selected from the group consisting of an α-tocopherol group and a trolox group.

12. A method of treating androgen-dependent malignant neoplasms, said method comprising administering an effective amount of an androgen having at least one substituent providing radical trapping properties to an individual having said androgen-dependent malignant neoplasms, wherein said at least one substituent is selected from the group consisting of an α-tocopherol group and a trolox group.

* * * * *